(12) United States Patent
Westerbeck

(10) Patent No.: US 6,336,911 B1
(45) Date of Patent: Jan. 8, 2002

(54) THERMAL SENSOR FOR HYPERTHERMIA SYSTEM

(75) Inventor: Todd L. Westerbeck, Burnsville, MN (US)

(73) Assignee: First Circle Medical, Inc., Minneapolis, MN (US)

( * ) Notice: Subject to any disclaimer, the term of this patent is extended or adjusted under 35 U.S.C. 154(b) by 0 days.

(21) Appl. No.: 09/334,520

(22) Filed: Jun. 16, 1999

(51) Int. Cl.[7] .......................... A61M 37/00; A61F 7/12; A61F 1/14; G01D 21/00

(52) U.S. Cl. ..................... 604/6.13; 604/4.01; 604/113; 422/44; 422/82.12; 73/866.5; 73/DIG. 8

(58) Field of Search ................ 604/4.01–6.16, 604/113; 422/44, 46, 68.1, 82.12; 600/300–301, 366, 368, 412, 415, 438–439, 468, 549; 601/1, 3; 73/866.5, 432.1, DIG. 8; 210/645, 739, 742

(56) References Cited

U.S. PATENT DOCUMENTS

| | | | |
|---|---|---|---|
| 4,298,006 A | | 11/1981 | Parks |
| 5,391,142 A | | 2/1995 | Sites et al. |
| 5,628,565 A | * | 5/1997 | Hagen et al. |
| 5,653,538 A | * | 8/1997 | Phillips ....................... 274/138 |
| 5,730,720 A | * | 3/1998 | Sites et al. |
| 5,733,398 A | * | 3/1998 | Carson et al. ................ 156/69 |
| 5,780,737 A | * | 7/1998 | Wible et al. |
| 6,023,969 A | * | 2/2000 | Feller ....................... 73/204.25 |

OTHER PUBLICATIONS

"Extracorporeal Whole Body Hyperthermia," First Circle Medical, Inc., Doc. No. 160002, 1999.

* cited by examiner

Primary Examiner—Angela D. Sykes
Assistant Examiner—Patricia Bianco
(74) Attorney, Agent, or Firm—Popovich & Wiles, P.A.

(57) ABSTRACT

The invention provides a temperature probe comprising an inlet end opposed to an outlet end; a flow-directing passage defined by a wall; the wall, the inlet end, and the outlet end configured to define a longitudinal axis; a strut attached to the wall at an attachment site, and a temperature sensor located at the distal tip of the strut to position the sensor in the flow of fluid along the longitudinal axis through the passage, wherein the distance from the inlet end to the sensor is less than the distance from the inlet end to the attachment site.

10 Claims, 2 Drawing Sheets

THERMAL SENSOR FOR HYPERTHERMIA SYSTEM

FIELD OF THE INVENTION

The present invention relates generally to hyperthermia systems and more particularly to in-line blood temperature monitoring devices for use during a hyperthermia procedure.

BACKGROUND OF THE INVENTION

Whole body hyperthermia is a disease treatment technique or therapy that has been used to treat a number of diseases. In operation, blood is removed from the body and heated externally to a target temperature and then returned to the body. Various treatment protocols have been proposed and several studies are directed to assessing the efficacy of the therapy for several disease indications. Suitable structures for carrying out whole body hyperthermia are known from U.S. Pat. No. 5,391,142 to Sites et al., incorporated herein by reference. A microprocessor-based hyperthermia is known from the Optichem SLH 100 system. Although the efficacy of the therapy is now established, there is a continuing need to improve the devices used to carry out this procedure. One particular problem relates to body temperature estimation. In general, the return of heated blood to the body is met with compensatory mechanisms which attempt to cool the body. Conventional thermal sensors are marginal and there is a need for improved temperature monitoring devices for carrying out hyperthermia.

SUMMARY OF THE INVENTION

The present invention improves the ability to control the blood and body temperature. An improved temperature monitoring device is especially well suited to extracorporeal whole body hyperthermia, but may be useful in other patient care settings as well.

The sensor disclosed is connected to the blood flow circuit near the patient. The temperature sensor has a very small mass and is placed on a strut. The strut places the thermal sensor in the laminar blood flow of a duct or fitting. In this fashion, a fast reacting thermal assessment may be made of blood temperature as blood enters or leaves the body.

BRIEF DESCRIPTION OF THE DRAWINGS

An exemplary version of a thermal sensor is shown in the figures wherein like reference numerals refer to equivalent structure throughout, and wherein.

DETAILED DESCRIPTION OF PREFERRED EMBODIMENT(S)

Figure 1:
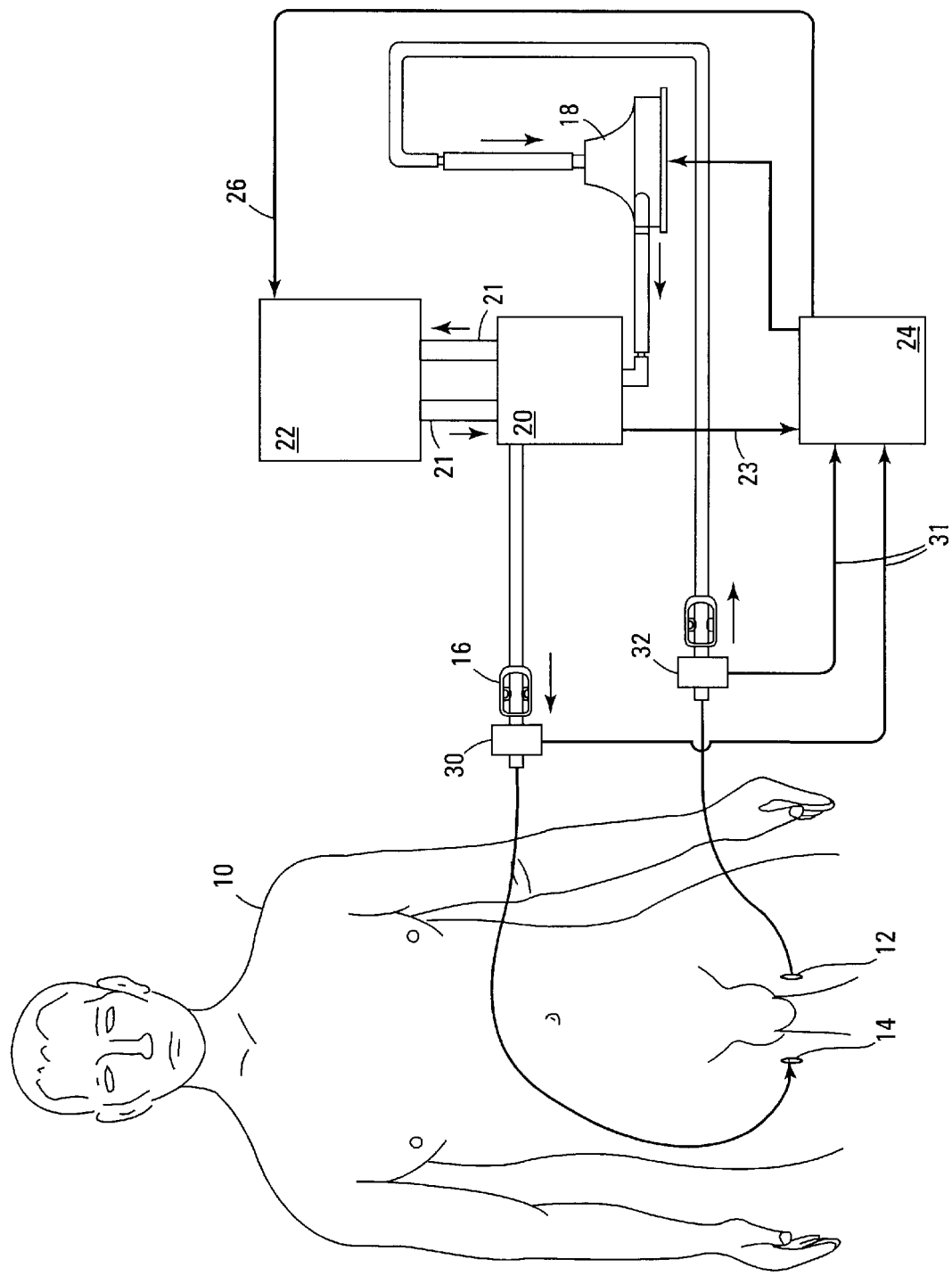
FIG. 1 is a schematic diagram of a simplified hyperthermia system.

FIG. 1 shows a patient 10 undergoing a perfusion treatment for whole body hyperthermia. Blood is withdrawn from a first venous cutdown 12 in the leg. The blood, after extracorporeal treatment, is returned to another venous cutdown 14 in the other leg. Venous to venous transport is preferred although the site of entry and exit is primarily a matter of medical judgment. It may be noted that a single cannula can be used to both withdraw and return blood if such a system is available. The connections to the patient are controlled by conventional clamps, such as those depicted by clamp 16. The blood is moved through the hyperthermia system by a blood pump 18 of conventional construction. Both peristaltic and centrifugal pumps are used for this purpose. The blood is heated in a heat exchanger 20 placed in the perfusion circulation system. In this particular system, a heated water supply 22 selectively supplies heated water to the heat exchanger 20 through connections depicted at 21.

A computer-based controller 24 receives temperature information from the heat exchanger 20 through an appropriate connection shown as connection 23. The controller 24 sends temperature control information to the heated water supply 22 via connection 26. The controller 24 may control water temperature using either open loop or closed loop control methods. The computer controller 24 receives body temperature information from one or more temperature sensors 30, 32 located as near the patient as practical. In some configurations the sensors may be incorporated in the cannulating devices themselves. The connections between the sensors and the controller are shown by cabling 31.

Figure 2:
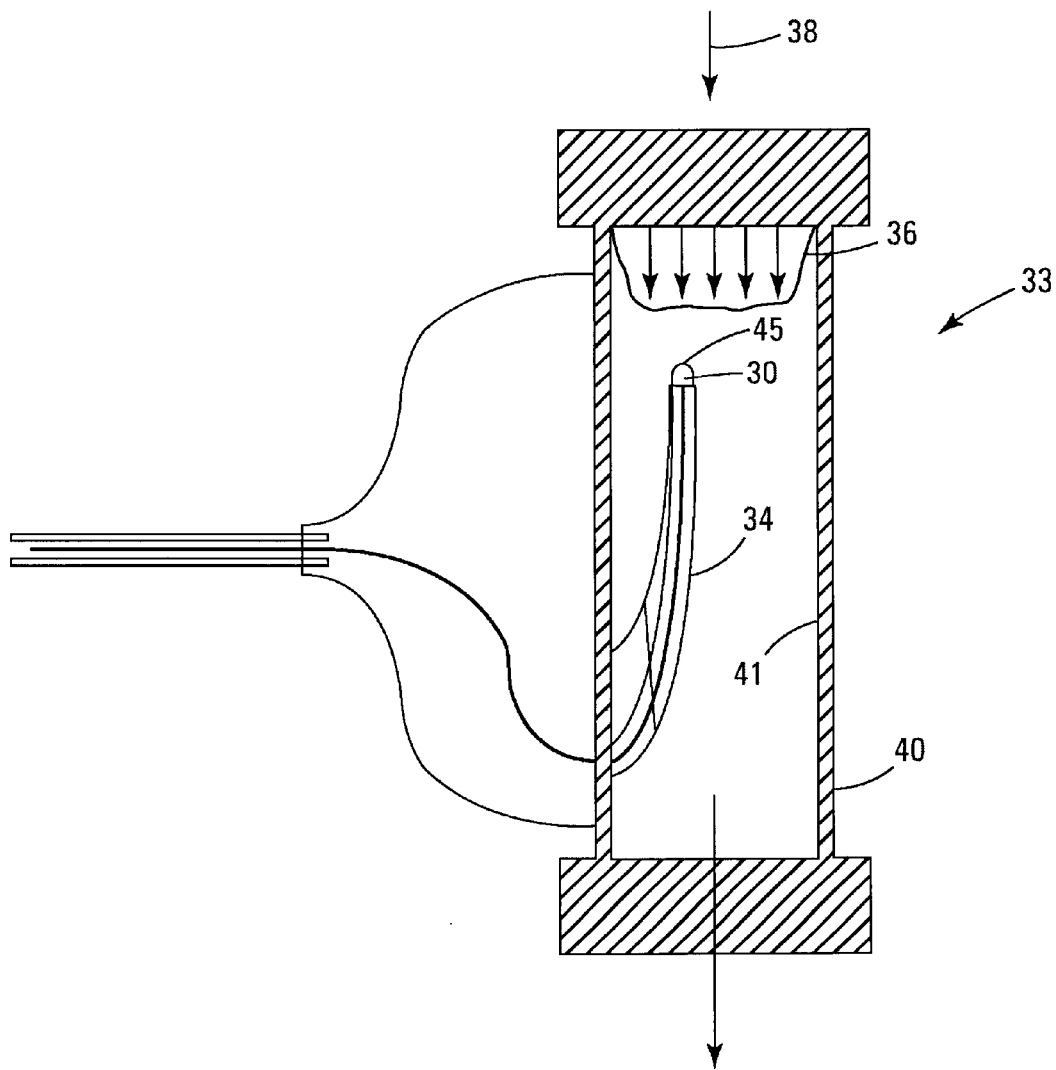
FIG. 2 is a cross-section of an exemplary temperature sensor.

FIG. 2 illustrates a temperature probe 33 for supporting the temperature sensor 30 in the flow of blood moving through the hyperthermia system. As shown in FIG. 2, the probe 33 includes a tube or flow-directing passage 40 having a wall defining an interior lumen 41. Although a cylindrical shape is shown and is preferred to minimize wetted surface area, other cross-sectional shapes are operable. As shown in FIG. 2, the cross-sectional area of the lumen 41 remains constant in the direction of flow indicated by arrow 38. It should be appreciated that the lumen 41 may decrease in cross-sectional area in the direction of flow to maintain laminar flow past the strut 34.

A temperature sensor 30 is attached to the strut 34. Preferably, the strut 34 is shaped and positioned such that the sensor 30 supported thereon is placed in a region of laminar flow and preferably near a location of maximum flow velocity. A region of laminar flow is illustrated in the velocity profile 36. More specifically, the strut 34 is shaped and positioned such that at least a portion of strut 34 lies upstream of the site at which the strut 34 attaches to or passes through the tube 40. The preferred strut 34 has a generally arcuate shape along its length. As shown in the embodiment illustrated in FIG. 2, the strut 34 has a terminating tip 45 that is positioned near the axial center of the tube 40 where the blood flow achieves maximum velocity. In this fashion the sensor 30 is located in the maximum flow zone in the device and can sense subtle changes in blood temperature. By positioning the sensor "in-line", or in the flow of blood as it passes through the system, advantages are achieved. For example, the laminar flow prevents disruption of the blood and temperature change due to mixing. This factor combined with the fast response small thermal mass sensor 30 improves control of body temperature.

The preferred form of the probe 33 includes fittings which may be barbed. These allow the device to be positioned close to the patient. It is believed that monitoring in close proximity to the patient is desirable to minimize heat loss to the environment.

In the embodiment of a hyperthermic system illustrated in FIG. 1, a second in-flow temperature sensor 32 is shown. The use of a second sensor increases the ability of the system to accurately monitor and control temperature. This sensor 32 is preferably supported in the line of blood flow by a probe substantially the same as probe 33 described above and illustrated in FIG. 2.

The sensors 30 and 32 may be of any temperature-sensing type, such as thermistors, thermocouples, and the like.

Although an illustrative version of the device is shown, it should be clear that many modifications to the device may be made without departing from the scope of the invention.

What is claimed is:

1. A temperature probe comprising:
   an inlet end opposed to an outlet end;
   a flow-directing passage defined by a wall;
   the wall, the inlet end, and the outlet end configured to define a longitudinal axis;
   a strut attached to said wall at an attachment site; and
   a temperature sensor located at the distal tip of said strut to position the sensor in the flow of fluid along the longitudinal axis through the passage,
   wherein the distance from said inlet end to said sensor is less than the distance from said inlet end to said attachment site.

2. A temperature probe according to claim 1 having a first axis perpendicular to the longitudinal axis and wherein said temperature sensor is located near the center of the first axis of said flow-directing passage.

3. A hyperthermia system comprising:
   a) a device for drawing blood from a patient;
   b) a device for extracorporeal heating of the drawn blood;
   c) a device for monitoring and controlling the heating of the drawn blood including a temperature probe positioned in the extracorporeal flow of blood, said probe comprising:
      an inlet end opposed to an outlet end;
      a flow-directing passage defined by a wall;
      the wall, the inlet end, and the outlet end configured to define a longitudinal axis;
      a strut attached to said wall at an attachment site; and
      a temperature sensor located at the distal tip of said strut to position the sensor in the flow of blood along the longitudinal axis through the passage,
      wherein the distance from said inlet end to said sensor is less than the distance from said inlet end to said attachment site; and
   d) a device for returning drawn blood to the patient.

4. A hyperthermia system according to claim 3, said hyperthermia system further comprising:
   e) a second temperature probe in the extracorporeal flow of blood, said second probe comprising:
      a second inlet end;
      a second outlet end;
      a second flow-directing passage defined by a second wall;
      a second strut attached to said wall at a second attachment site; and
      a second temperature sensor located at the distal tip of said second strut, to position the second sensor in the flow of blood through the second passage.
   wherein the distance from said second inlet end to said second sensor is less than the distance from said second inlet end to said second attachment site; and
   wherein one of said temperature sensors is positioned in-line upstream of said device for extracorporeal heating and senses the temperature of blood as it is removed from the patient and before it is heated, and the other said temperature sensor is positioned in-line downstream of said device for extracorporeal heating and monitors the temperature of blood after it is heated and before it is returned to the patient.

5. A hyperthermia system according to claim 3 having a first axis perpendicular to the longitudinal axis and wherein said temperature sensor is located near the center of the first axis of said flow-directing passage.

6. A hyperthermia system comprising:
   a) a first cannula inserted into a cutdown in a patient for drawing blood therefrom;
   b) a pump in fluid communication with said cannula for drawing blood from the patient and through the system;
   c) heat exchanger in fluid communication with said cannula and pump for extracorporeal heating of the drawn blood;
   d) a temperature probe positioned in the extracorporeal flow of blood, said probe comprising:
      an inlet end opposed to an outlet end;
      a flow-directing passage defined by a wall;
      the wall, the inlet end, and the outlet end configured to define a longitudinal axis;
      a strut attached to said wall at an attachment site; and
      a temperature sensor located at the distal tip of said strut to position the sensor in the flow of blood along the longitudinal axis through the passage,
      wherein the distance from said inlet end to said sensor is less than the distance from said inlet end to said attachment site; and
   e) a second cannula inserted into a cutdown in a patient for returning drawn blood to the patient, said second cannula being in fluid communication with said first cannula, said pump and said heat exchanger.

7. A hyperthermia system according to claim 6 having a first axis perpendicular to the longitudinal axis and wherein said temperature sensor is located near the center of the first axis of said flow-directing passage.

8. A method of heating blood in a hyperthermia system comprising the steps of:
   a) providing a hyperthermia system incorporating an in-line temperature probe for sensing the temperature of blood as it flows through the system, said probe comprising:
      an inlet end opposed to an outlet end;
      a flow-directing passage defined by a wall;
      the wall, the inlet end, and the outlet end configured to define a longitudinal axis;
      a strut attached to said wall at an attachment site; and
      a temperature sensor located at the distal tip of said strut to position the sensor in the flow of blood along the longitudinal axis through the passage,
      wherein the distance from said inlet end to said sensor is less than the distance from said inlet end to said attachment site;
   b) drawing blood from a patient;
   c) sensing the temperature of the drawn blood before it is heated using said in-line temperature probe;
   d) heating the drawn blood; and
   e) returning the heated blood to the patient.

9. A method according to claim 8 further comprising the steps of:
   f) providing a second in-line temperature probe positioned in the extracorporeal flow of blood, said second probe comprising:
      a second inlet end,
      a second outlet end;
      a second flow-directing passage defined by a second wall;
      a second strut attached to said wall at a second attachment site; and
      a second temperature sensor located at the distal tip of said strut,
      to position the second sensor in the flow of blood through the second passage, wherein the distance from said second inlet end to said second sensor is less than the distance from said second inlet end to said second attachment site; and g) sensing the temperature of after it is heated and before it is returned to the patient using said second temperature probe.

10. A method according to claim 8 having a first axis perpendicular to the longitudinal axis and wherein said temperature sensor is located near the center of the first axis of said flow-directing passage.

* * * * *